United States Patent
Tamura et al.

(10) Patent No.: US 7,022,676 B2
(45) Date of Patent: Apr. 4, 2006

(54) PEPTIDE HAVING ANGIOTENSIN CONVERTING ENZYME INHIBITORY EFFECT

(75) Inventors: Yoshitaka Tamura, Zama (JP); Hiroshi Miyakawa, Zama (JP); Akio Yamada, Zama (JP); Hitoshi Saito, Zama (JP); Yasushi Kawaguchi, Zama (JP); Hiroshi Ochi, Zama (JP); Tomoko Ide, Zama (JP); Eri Inoue, Zama (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 0 days.

(21) Appl. No.: 10/496,200

(22) PCT Filed: Nov. 21, 2002

(86) PCT No.: PCT/JP02/12197

§ 371 (c)(1),
(2), (4) Date: May 20, 2004

(87) PCT Pub. No.: WO03/044044

PCT Pub. Date: May 30, 2003

(65) Prior Publication Data

US 2005/0004041 A1     Jan. 6, 2005

(30) Foreign Application Priority Data

Nov. 21, 2001 (JP) .............................. 2001-355923

(51) Int. Cl.
*A61K 38/00* (2006.01)
(52) U.S. Cl. ....................................................... 514/18
(58) Field of Classification Search .................. 514/18
See application file for complete search history.

(56) References Cited

FOREIGN PATENT DOCUMENTS

| JP | 7-313185 | 12/1995 |
|---|---|---|
| JP | 11-343297 | 12/1999 |

OTHER PUBLICATIONS

Maeno et al, Identification of an Antihypertensive Peptide from Casein Hydrolysate Produced by a Proteinase from *Lactobacillus helveticus* CP790, Journal of Dairy Science (1996), vol. 79, 1316-1321.*

* cited by examiner

*Primary Examiner*—Bruce R. Campell
*Assistant Examiner*—Thomas S. Heard
(74) *Attorney, Agent, or Firm*—Knobbe, Martens, Olson & Bear, LLP

(57) ABSTRACT

A peptide Met-Lys-Pro, which is obtained by chemical synthesis ot hydrolysis of casein, is used as the active ingredient of angiotensin converting enzyme inhibitors or hypotensive drugs.

4 Claims, 1 Drawing Sheet

PEPTIDE HAVING ANGIOTENSIN CONVERTING ENZYME INHIBITORY EFFECT

RELATED APPLICATIONS

This application is the U.S. National Phase under 35 U.S.C. 517 371 of International Application PCT/JP02/12197, filed Nov. 21, 2002, which was published in a language other than English and claims priority of JP 2001-355923, filed Nov. 21, 2001. Each of the above applications are incorporated herein by reference in their entirety.

TECHNICAL FIELD

The present invention relates to a novel peptide and an angiotensin converting enzyme inhibitor containing the peptide. The angiotensin converting enzyme inhibitor can be used as food products, feeding stuffs and pharmaceuticals.

BACKGROUND ART

Angiotensin converting enzyme (ACE) is an enzyme that acts on angiotensin I which is generated from angiotensinogen by digestion with renin and converts it to angiotensin II by releasing two amino acids in the C-terminal thereof. The angiotensin converting enzyme not only acts on producing angiotensin II that has a strong hypertensive effect but also acts on inactivating bradykinin that has a hypotensive effect. From those actions, angiotensin converting enzyme inhibitors have been used as therapeutic agents for hypertension, and, for example, Captopril (produced by Sankyo Co., Ltd.) and Renivase (produced by Banyu Pharmaceutical Co., Ltd.) have been known as commercially available drugs. In addition, it is also known that the angiotensin converting enzyme inhibitors have an effect of making cardiac hypertrophy regress.

On the other hand, peptides having angiotensin converting enzyme inhibitory effects have been found in natural products or in enzyme-degraded products of animal proteins such as casein and gelatin, vegetable proteins such as those from wheat, rice and corn, and fish proteins such as those from sardine. For instance, the known peptides found in natural products include teprotide (nonapeptide, SQ20881) and metabolite IS83 of Actinomyces bacterium belonging to the genus *Streptomyces* (JP 58-177920 A). In addition, the known enzyme-degraded products include peptides obtained by decomposing casein with trypsin (JP 58-109425 A, JP 59-44323 A, JP 59-44324 A, JP 61-36226 A, and JP 61-36227 A), peptides obtained by hydrolyzing casein with thermolysin (JP 6-277090 A, JP 6-277091 A, JP 6-279491A, JP 7-101982A, and JP 7-101985A), peptides obtained by hydrolyzing casein or the like with lactic bacteria or a combination of proteinases and peptidases (JP 6-197786 A, JP 6-40944 A, and JP 2001-136995 A (which are hereinafter referred to as "References 1 to 3", respectively) The peptides of References 1 to 3 are used as foods for specified health use having the hypotensive effect.

Among the peptides described above, the peptide described in JP 7-101982 A (hereinafter, referred to as "Reference 4") shows the highest inhibitory activity against angiotensin converting enzyme and has a comparatively simple structure of tripeptide.

DISCLOSURE OF THE INVENTION

As described above, various angiotensin converting enzyme inhibitory peptides have been known in the art. However, those peptides are still insufficient in inhibitory activity against angiotensin converting enzyme as a function in food products. Thus, it has been desired to obtain a peptide derived from a natural product having a higher inhibitory activity against angiotensin converting enzyme and also having a simple structure and to apply such a peptide to food products, pharmaceuticals, or the like.

The inventors of the present invention have made extensive studies to solve the above problem, and as a result, they found out that hydrolysis of casein with a specific enzyme forms a novel peptide having a high inhibitory activity against angiotensin converting enzyme in the hydrolysate and the peptide has a sequence represented by Met-Lys-Pro, and thereby completed the present invention.

That is, the present invention relates to a peptide consisting of Met-Lys-Pro (hereinafter also referred to as "peptide of the present invention").

Further, the present invention provides an angiotensin converting enzyme inhibitor including a peptide consisting of Met-Lys-Pro as an effective ingredient.

Further, the present invention provides a hypotensive agent including a peptide consisting of Met-Lys-Pro as an effective ingredient.

Hereinafter, the present invention will be described in detail.

The peptide of the present invention has a sequence represented by Met-Lys-Pro. In addition, the peptide of the present invention maybe the salts of the peptide. In the present invention, Met denotes an L-methionine residue, Lys denotes an L-lysine residue and Pro denotes an L-proline residue.

The peptide of the present invention can be produced by hydrolyzing a protein such as casein with an appropriate hydrolase.

Hereinafter, a method of hydrolyzing a protein with a hydrolase will be exemplified.

For the hydrolysis of a protein with an enzyme, although the manner of treatment varies depending on properties of a protein, a material protein is dispersed in cold water or heated water and dissolved therein when the protein is soluble. When the protein has poor solubility, it is mixed with hot water and homogenized while vigorously stirring.

The protein is not specifically limited as far as it contains a sequence represented by Met-Lys-Pro and produces the peptide of the present invention when it is digested with an appropriate hydrolase. Thus, any protein originated from an animal or bacteria may be used. In particular, a preferable protein is casein that is available in bulk.

It is desirable to sterilize a solution containing the protein at 70 to 90° C. for approximately 15 seconds to 10 minutes in view of preventing the deterioration by bacterial pollution.

Subsequently, it is preferable to adjust pH of the protein-containing solution to optimum pH for a hydrolase used or proximal pH thereof by adding a basic agent or an acidic agent to the solution. The basic or acidic agent used in the method of the present invention may be any basic or acidic agent as far as it is acceptable in food products or pharmaceuticals. Specific examples of the basic agents include sodium hydroxide, potassium hydroxide, and potassium carbonate and the acidic agents include hydrochloric acid, citric acid, phosphoric acid, and acetic acid.

Next, a predetermined amount of a hydrolase is added to the protein solution to carry out a reaction at a temperature of approximately 10 to 85° C. for 0.1 to 48 hours.

The hydrolase is preferably an endopeptidase, although not specifically limited as far as the hydrolase can hydrolyze the protein to generate the peptide of the present invention. The endopeptidases include a protease originated from *Bacillus* bacteria and a protease originated from animal pancreases. Those enzymes are commercially available. Preferable protease originated from *Bacillus* bacteria can be exemplified by Biopuraze sp-20 (manufactured by Nagase Biochemical Industry Inc.) and Protease N (manufactured by Amano Enzyme Inc.), while preferable protease originated from animal pancreases can be exemplified by PTN6.0S (manufactured by Novozymes Japan Ltd.). The protease originated from *Bacillus* bacteria is desirably added at a rate of 100 to 5000 active units per 1 gram of protein. On the other hand, the protease originated from animal pancreases is desirably added at a rate of 3000 to 8000 active units per 1 gram of protein.

The hydrolase used in the present invention may be one kind of hydrolase or a combination of two or more kinds. When two or more hydrolases are used, their enzyme reactions may be carried out simultaneously or independently. In the present invention, particularly preferable is to use a mixture of Biopuraze sp-20, Protease N, and PTN6.0S.

A solution in which an enzyme is added is kept at an appropriate temperature depending on the type of the enzyme, for example, 30 to 60° C., preferably 45 to 55° C. to initiate the hydrolysis of the protein. Regarding the reaction time of hydrolysis, the reaction is continued until a preferable decomposition rate is attained while the decomposition rate of the reaction is monitored. For obtaining the peptide of the present invention, the decomposition rate of 20 to 30% is desirable.

As for a method of calculating the decomposition rate of the protein, the total nitrogen content of a sample is determined by the Kjeldahl method (The Japanese Society for Food Science and Technology, Ed., "Food Analysis Method", page 102, KORIN Publishing Co., Ltd., 1984) and the content of formol nitrogen in the sample is determined by the formol titration method (Manda et al., Ed., "Laboratory Manuals of Food Engineering", First Volume, page 547, Yokendo Co., Ltd., 1970), followed by calculating the decomposition rate with the following equation using those measurements.

Decomposition rate (%)=(Formol nitrogen content/ Total nitrogen content)×100

The termination of the enzyme reaction is, for example, performed by deactivation of the enzyme in the hydrolysis solution. It can be carried out by heat deactivation using the general method. The conditions for sufficient deactivation can be suitably determined with respect to a heating temperature and a retention time of the heat deactivation in consideration of a thermal stability of the enzyme used. For example, it can be carried out in a temperature range of 80 to 130° C. for a retention time of 30 minutes to 2 seconds.

From the above hydrolysis solution, preferably, the peptide of the present invention is isolated and purified. The purification of the peptide is generally performed by the same technique as one employed in the purification of an oligopeptide, for example, by appropriately combining various kinds of chromatography including ion-exchange chromatography, absorption chromatography, reversed phase chromatography, distribution chromatography and gel filtration chromatography, solvent precipitation, extracting by salting, and distribution between two liquid phases etc. At the time of purifying the peptide of the present invention, fractions containing objective materials can be determined based on an angiotensin converting enzyme inhibitory effect described below. Active ingredients in those fractions can be identified by mass spectrometry.

Furthermore, the peptide of the present invention can be also produced by chemical synthesis. The chemical synthesis of the peptide of the present invention can be carried out by a liquid phase method or a solid phase method, which are generally used for the synthesis of an oligopeptide. The synthesized peptide is deprotected if required, and then unreacted reagents, byproducts, and so on are removed. Such peptide synthesis can be carried out using a commercially available peptide synthesizer. The production of the target peptide can be confirmed based on an angiotensin converting enzyme inhibitory effect.

The peptide of the present invention can be used as an effective ingredient of an angiotensin converting enzyme inhibitor. The peptide of the present invention has an inhibitory effect on angiotensin converting enzyme and a suppressing effect on bradykinin inactivation and exhibits a hypotensive effect. Therefore, it can be used as a preventive agent or a therapeutic agent against various diseases derived from hypertension, such as cerebral hemorrhage, cerebral infarction, angina pectoris, myocardial infarction, and renal insufficiency, more specifically, it can be used as a hypotensive agent or the like. In addition, it is known that the angiotensin converting enzyme inhibitor also has effects on instinct hypertension whose cause is unknown, so that the peptide of the present invention is also expected to show a therapeutic or preventive effect on the instinct hypertension. In addition, it can be used as a therapeutic or preventive drug for other diseases such as cardiac hypertrophy and angina illness, on which the angiotensin converting enzyme inhibitor is considered to be effective.

The angiotensin converting enzyme inhibitor of the present invention may be administered either orally or parenterally, but the oral administration is preferable. The parenteral administration includes intravenous injection, intrarectal administration, and inhalation. The pharmaceutical forms for the oral administration include a tablet form, a capsule form, a troche form, a syrup form, a granule form, a powder form, and an ointment form. Upon pharmaceutical formulation, in addition to a whey protein hydrolysate, other ingredients such as an excipient, a pH regulator, a colorant, and a flavoring agent for drugs, which are generally used for the conventional pharmaceutical formulation, can be used. Furthermore, any drug known in the art or to be found out in future, which has an angiotensin converting enzyme inhibitory effect can be also used together.

The peptide of the present invention may be contained as an effective ingredient in a food product and, as an embodiment of the angiotensin converting enzyme inhibitor, processed into a food product having an angiotensin converting enzyme inhibitory effect. Irrespective of the forms of liquid, paste, solid, and powder etc., those food products include: in addition to candies, fluid diets, and feeding stuffs (including those for pet animals), wheat flour products such as bread, macaroni, spaghetti, noodles, bread mix, french-fry mix, and bread crumb; instant foods such as instant noodles, cup noodles, retort-packed foods, prepared foods, canned foods, microwave meals, instant soup or stew, instant miso soup or Japanese clean soup, canned soup, freeze-dried foods and other instant foods; agricultural processed products such as canned farm products, canned fruits, jam or marmalade, pickles, boiled beans, agricultural dry foods, and cereals (grain-processed products); processed marine products such as canned marine products, fish hams or sausages, fish paste, marine product dainties, and tsukudanis; stock farm-processed products such as canned stockbreeding products, pastes, and stockbreeding flesh hams or sausages; milk and milk products such as processed milk, milk beverages, yogurt, lactic acid bacteria beverages, cheese, ice cream, modified dry milk, cream and other milk products; fats and fatty oils such as butter, margarine, and vegetable oils; basic seasonings such as soy sauce, miso, sauces, tomato-processed seasonings, sweet cooking rice wines, and vinegar; complex seasonings and foods such as cooking mix, curry premix, bastes, dressings, noodle soups, spices and other complex seasonings; frozen foods such as material frozen foods, half-prepared frozen foods, and cooking-finished frozen foods; confectioneries such as caramels, candies, chewing gums, chocolates, cookies, biscuits, cakes, pies, snacks, crackers, Japanese sweets, rice biscuits, beans confectionery, desserts and other confectioneries; beverages of taste such as carbonated drinks, natural fruit juices, fruit juice drink, soft drink that contains fruit juice, pulp drink, fruit drink that contains berries, vegetable drink, soybean milk, soybean milk drink, coffee drink, tea drink, powder drink, concentrated drink, sports drink, nutrition drink, and alcoholic beverages and other beverages of taste; and other food products on the market such as baby foods, fish flour, and boiled rice with tea paste.

In the angiotensin converting enzyme inhibitor of the present invention, the content of the peptide of the present invention is preferably at least 0.001% by weight with respect to the final composition of the angiotensin converting enzyme inhibitor.

The dosage of the angiotensin converting enzyme inhibitor of the present invention varies depending on ages, symptoms, and so on. In general, however, the inhibitor is administered at the dosage of 0.001 to 3000 mg/day, preferably 0.01 to 30 mg/day, further, it may be administered either once a day or two or three times a day.

BEST MODE FOR CARRYING OUT THE INVENTION

Figure 1:
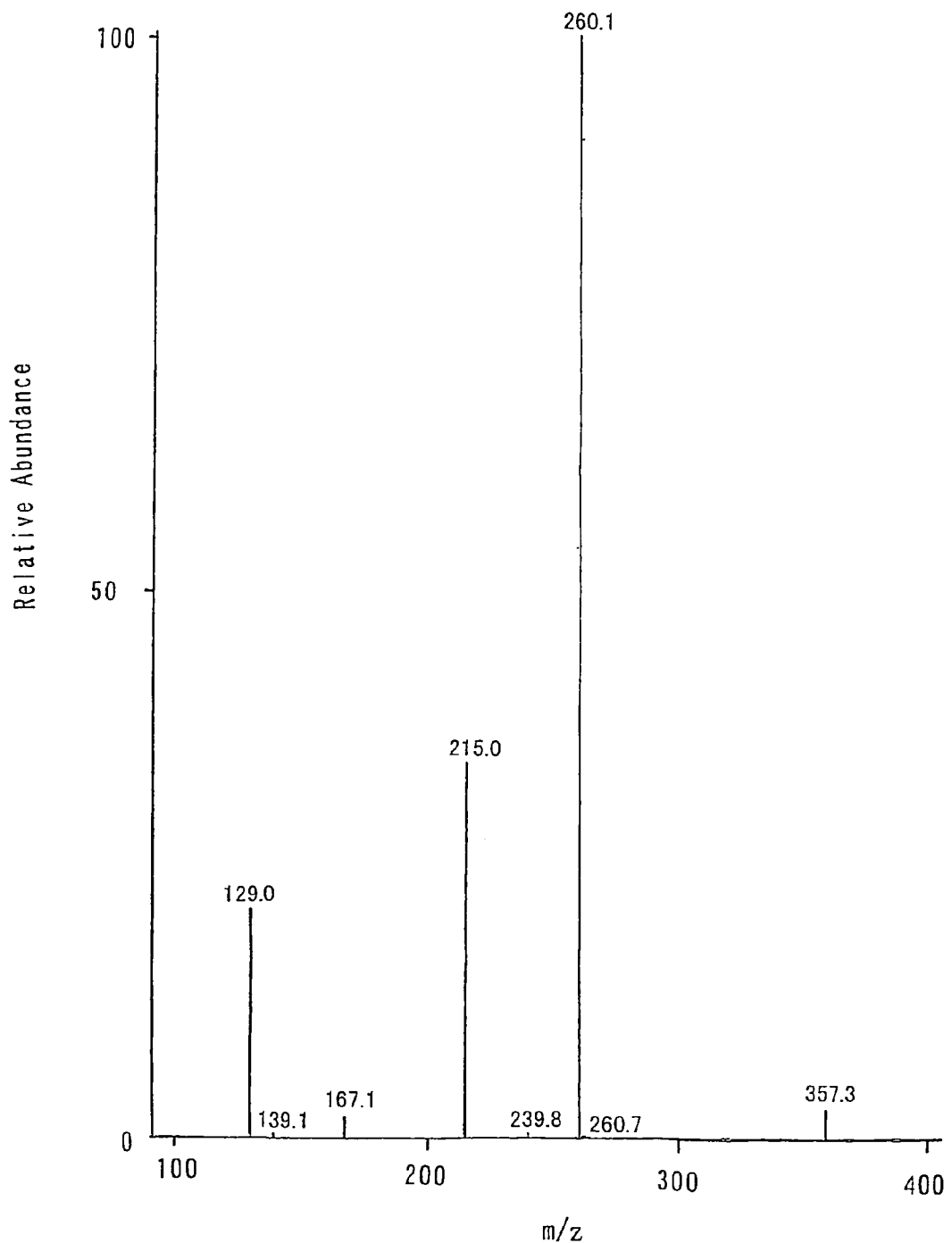
FIG. 1 illustrates results of an MS/MS analysis on a peptide of the present invention.

Next, the present invention will be described in more detail with examples.

EXAMPLE 1

Production of Peptide by Enzyme Dedratation of Casein

<1> Enzyme Degradation of Casein 900 g of water was added to 100 g of commercially available casein (manufactured by New Zealand Dairy Board) and the casein was dispersed therein well. Then, pH of the resultant solution was adjusted to 7.0 by the addition of sodium hydroxide to dissolve the casein completely and thereby, an aqueous solution of casein at a concentration of about 10% was prepared. The aqueous solution of casein was heat-sterilized at 85° C. for 10 minutes and then adjusted to a temperature of 50° C., followed by adjusting the pH thereof to 9.5 by the addition of sodium hydroxide.

After that, 100, 800 active units (1,200 active units per 1 gram of protein) of Biopuraze sp-20 (manufactured by Nagase Biochemical Industry Inc.), 168,000 active units (2,000 active units per 1 gram of protein) of Protease N (manufactured by Amano Enzyme Inc.), and 588,000 active units (7,000 active units per 1 gram of protein) of PTN6.0S (manufactured by Novozymes Japan Ltd.) were added to the solution to initiate a hydrolysis reaction. When the decomposition rate of casein reached to 24.1%, the enzyme was deactivated by heating at 80° C. for 6 minutes to terminate the enzyme reaction, and followed by cooling to 10° C. This hydrolysis solution was extra-filtrated by an extra-filtration membrane (manufactured by Asahi Kasei Corporation) of a fraction molecular weight of 3,000, and then it was concentrated and followed by freeze-drying, which resulted in 85 g of a freeze-dried product.

<2> Isolation of Peptide by HPLC

The casein hydrolysate was separated by a reverse phase HPLC. The conditions of the HPLC are described in HPLC Condition 1 described below.

[HPLC Condition 1]
Column: CAPCELL PAK C18 (UG120, 5 μm)
　20 mm I.D.×250 mm (Shiseido Co., Ltd.)
Detection: UV 215 nm
Flow rate: 16 ml/min
Eluent A: 1% acetonitrile aqueous solution containing 0.05% TFA
Eluent B: 25% acetonitrile aqueous solution containing 0.05% TFA Under the linear gradient condition from 100% of Eluent A to 100% of Eluent B after 40 minutes, a hydrolysate was separated. For each eluted fraction, the angiotensin converting enzyme inhibitory ability was determined by the method described later. As a result, a peptide having the angiotensin converting enzyme inhibitory ability was eluted at a retention time of 22 minutes. For purifying the peptide, it was further purified by HPLC. This condition is represented below as HPLC Condition 2.

[HPLC Condition 2]
Column: CAPCELL PAK C18 (UG300, 5 μm)
　2.0 mm I.D.×250 mm (Shiseido Co., Ltd.)
Detection: UV 215 nm
Flow rate: 0.2 ml/min
Eluent A: 1% acetonitrile aqueous solution containing 0.05% TFA
Eluent B: 10% acetonitrile aqueous solution containing 0.05% TFA Under the linear gradient condition from 100% of Eluent A to 100% of Eluent B after 15 minutes, the strong angiotensin converting enzyme inhibitory ability was observed at a peak of a retention time of 13 minutes. The angiotensin I converting enzyme inhibitory ability at this peak was such that IC50 [a concentration (μg/ml) required for inhibiting 50% of the angiotensin converting enzyme activity]=0.18 μg/ml.

The compound in the above activity peak was identified by the protein sequencer (Model-473A) of Applied Biosystems Ltd. As a result, it was found that the compound had a novel structure of Met-Lys-Pro. Furthermore, the molecular weight (M) was identified as 374.2 using the mass spectrometer LCQ from Thermoquest Co., Ltd., and daughter ions of m/z=260, 215, and 129 etc. were detected by the MS/MS analysis with a parent ion of m/z=375.2 (MH+) as shown in FIG. 1.

Consequently, it was elucidated that the structure of the peptide having an angiotensin converting enzyme inhibitory ability was H-Met-Lys-Pro-OH. 42.5 mg of a tripeptide Met-Lys-Pro was contained in the freeze-dried product (85 g).

EXAMPLE 2

Chemical Synthesis of Peptide

Using the peptide synthesizer (Model 433A, Applied Biosystems Ltd.) and also using Fmoc-L-Met (Applied Biosystems Ltd.), Fmoc-Lys (Boc) (Applied Biosystems Ltd.), and Fmoc-Pro-TrtA-PEG Resin (Watanabe Kagaku Kogyo K.K.) as raw materials, a tripeptide Met-Lys-Pro was synthesized by a solid phase synthesis method. The operation was performed according to the manual from Applied Biosystems Ltd., followed by deprotection. The peptide was purified under HPLC Condition 1 described above. As a result of the measurement of the angiotensin converting enzyme inhibitory ability using this material, almost the same value (IC50=0.19 μg/ml) as that of one extracted from the casein-degraded product obtained in Example 1 was obtained.

The molecular weight (M) of the obtained tripeptide was measured as 374.2 by the mass spectrometry. Almost the same spectrum as in FIG. 1 was obtained by the MS/MS analysis with the parent ion of mz=375.2 (MH+).

EXAMPLE 3

Angiotensin Converting Ensyme Inhibitory Effect of Peptide

The measurement of angiotensin converting enzyme inhibition was performed according to the Method of Cushman et al. [Biochemical Pharmacology vol. 20, pages 1637–1648 (1971)].

As samples, the peptides (Met-Lys-Pro) obtained in Example 1 and Example 2, peptides (Val-Pro-Pro, Ile-Pro-Pro) described in References 1 to 3, and peptide (Leu-Leu-Trp) described in Reference 4 were used. Each of those peptides was chemically synthesized in the same way as in Example 2.

The sample was dissolved in a 0.1M borate buffer (containing 0.3M NaCl, pH 8.3) and 0.08 ml thereof was then added in a tube. After that, 0.2 ml of an enzyme substrate (Hippuryl-histidyl-leucine, manufactured by Sigma Co., Ltd.) adjusted to 5 mM with the 0.1M borate buffer (containing 0.3M NaCl, pH 8.3) was added and then incubated at 37° C. for 3 minutes. Then, 0.02 ml of the rabbit lung angiotensin converting enzyme (manufactured by Sigma Co., Ltd.) adjusted to 0.1 U/ml by adding distilled water was added and then reacted at 37° C. for 30 minutes.

Subsequently, the reaction was terminated by adding 0.25 ml of 1N hydrochloric acid. Then, 1.7 ml of ethyl acetate was added and the mixture was stirred vigorously for 20 seconds, and centrifugation was performed at 3000 rpm for 10 minutes, followed by collecting 1.4 ml of an ethyl acetate layer. After removing a solvent by heating the obtained ethyl acetate layer, 1.0 ml of distilled water was added and the absorption (228 nm absorbance) of the extracted hippuric acid was measured and defined as an enzyme activity.

From the following equation, the inhibitory activity was calculated and then the IC50 [the concentration (μg/ml or μM) required for inhibiting 50% of angiotensin converting enzyme activity] was defined. The results are shown in Table 1.

Inhibition rate=$(A-B)/(A-C)\times100\%$

A: Enzyme activity (228 nm absorbance) in the case of containing no sample (peptide).

B: Enzyme activity (228 nm absorbance) when the sample was added.

C: Enzyme activity (228 nm absorbance) when the enzyme and the sample were not added.

TABLE 1

| Peptide | IC 50 (μM) |
| --- | --- |
| Peptide of Example 2 (Met-Lys-Pro) | 0.5 |
| Val-Pro-Pro | 6 |
| Ile-Pro-Pro | 4 |
| Leu-Leu-Trp | 2.2 |

EXAMPLE 4

Hypotensive Effect of Peptide on Animal

<1> Test Method

Twelve 10-week-old male SHR/Hos rats (purchased from Japan SLC, Inc.) were preliminary kept for 1 week and then the blood pressures of the rats were measured using the non-invasive automatic sphygmomanometer for small animal (MK-2000, manufactured by Muromachi Kikai Co., Ltd.).

The rats were divided into two groups each including 6 animals based on a systolic blood pressure so that mean systolic blood pressure of each group should be almost same value before administration. After that, the rats were fasted for about 16 hours. For the test group, the enzyme-degraded product of casein obtained in the section <1> of Example 1 was dissolved in water for injection and then orally administrated at a rate of 10 mL/kg body weight (100 mg/kg body weight for the enzyme-degraded product of casein and 0.05 mg/kg body weight for the peptide (Met-Lys-Pro) of the present invention). The blood pressure of the rats was measured 2 hours after the administration. For the control group, the same volume of water for injection was orally administered instead of the aqueous solution containing enzyme-degraded product of casein. The blood pressure of the rat was measured 2 hours after the administration.

<2> Test Results

The results are shown in Table 2. As is evident from Table 2, a drop in blood pressure was observed in the test group. On the other hand, it was not observed in the control group. Therefore, it was found that the enzyme-degraded product of casein containing the peptide (Met-Lys-Pro) of the present invention had a hypotensive effect on an animal.

TABLE 2

| | Systolic blood pressure before administration (mmHg) | Systolic blood pressure 2 hours after administration (mmHg) |
| --- | --- | --- |
| Test group | 182 | 140 |
| Control group | 184 | 177 |

EXAMPLE 5

Hypotensive Effect of Peptide on Human

<1> Test Method

Nine subjects were male volunteers at the age of 30 or more and less than 58 who suffered from mild hypertension showing systolic blood pressures of 140 to 165 mm Hg at the time of a screening test (medical examination by a doctor) 3 weeks before the initiation of uptake and who did not receive any treatment with hypotensive agent.

The subjects were divided into the test sample-uptake group of five subjects and the control group of four subjects so that the blood-pressure values measured at the time of the screening test, a habit of smoking and ages should be equalized between the groups.

3 g of the enzyme-degraded product of casein obtained in the section <1> of Example 1 (containing 1.5 mg of the peptide (Met-Lys-Pro) of the present invention) was taken as a test sample once a day, and 3 g of dextrin was taken as a control once a day. Blood pressure measurement (0–3rd weeks) was performed at almost the same time.

The obtained numerical values (systolic blood pressure) are shown in Tables 3 and 4.

The obtained numerical values (systolic blood pressure) were analyzed with respect to the significant difference thereof by the one way analysis of variation (see, for example, Kiyoshi Ichihara, "Statistics for Bioscience", Fifth Issue, Nankodo Co., Ltd., Nov. 20, 1991, p. 150–151) with a significant level of 5% using the statistical analysis software SPSS (manufactured by SPSS Inc.). When there was a significant difference in the values, mean values were compared by the Dunnett's multiple comparison method (see, for example, Kei Takeuchi and other 13 persons, Ed., "Statistics Dictionary", Toyo Keizai Inc., Dec. 4, 1989, p. 399).

TABLE 3

Results of test sample-uptake group
(Systolic blood pressure unit mmHg)

| No. | Before administration (0 week) | 1st week | 2nd week | 3rd week |
|---|---|---|---|---|
| 1 | 162 | 150 | 149 | 145 |
| 2 | 163 | 160 | 152 | 160 |
| 3 | 157 | 153 | 136 | 142 |
| 4 | 145 | 137 | 147 | 137 |
| 5 | 145 | 133 | 139 | 127 |

TABLE 4

Results of control group
(Systolic blood pressure unit mmHg)

| No. | Before administration (0 week) | 1st week | 2nd week | 3rd week |
|---|---|---|---|---|
| 1 | 150 | 145 | 139 | 144 |
| 2 | 153 | 145 | 136 | 156 |
| 3 | 149 | 137 | 134 | 135 |
| 4 | 146 | 143 | 148 | 137 |

>Test Results

As the results of the analysis with the statistical analysis software SPSS, there was found no significant difference in the control group at all of the 1st, 2nd, and 3rd weeks after the administration with respect to before the administration (0 week), while the results were obtained that there were the significant differences at the 2nd and 3rd weeks after the administration in the test sample-uptake group. Therefore, it was proved that the enzyme-degraded product of casein containing the peptide (Met-Lys-Pro) of the present invention had a hypotensive effect on human.

INDUSTRIAL APPLICABILITY

According to the present invention, there is provided a novel peptide useful as an angiotensin converting enzyme inhibitor. The peptide of the present invention is derived from a natural product and shows low toxicity and high safety. Thus, the peptide of the present invention can also be contained as the active ingredient in food products and, as an embodiment of the hypotensive agent, processed into food products having hypotensive effects.

What is claimed is:

1. A peptide consisting of Met-Lys-Pro.

2. An angiotensin converting enzyme inhibitor composition comprising the peptide of claim 1 as an effective ingredient.

3. A hypotensive agent comprising the peptide of claim 1 as an effective ingredient.

4. A pharmaceutical composition comprising the peptide of claim 1.

* * * * *

UNITED STATES PATENT AND TRADEMARK OFFICE
CERTIFICATE OF CORRECTION

PATENT NO. : 7,022,676 B2 Page 1 of 1
APPLICATION NO. : 10/496200
DATED : April 4, 2006
INVENTOR(S) : Tamura et al.

It is certified that error appears in the above-identified patent and that said Letters Patent is hereby corrected as shown below:

First Page, Abstract: line 2 "synthesis ot hydrolysis" should be changed to --synthesis or hydrolysis--

Column 1, Line 8, "U.S.C. 517 371" should be changed to --U.S.C. § 371--

Column 5, Line 53, "Peptide by Enzyme Dedratation" should be changed to --Peptide by Enzyme Degradation--

Column 7, Line 32, "Converting Ensyme Inhibitory" should be changed to --Converting Enzyme Inhibitory--

Signed and Sealed this

Nineteenth Day of September, 2006

JON W. DUDAS
*Director of the United States Patent and Trademark Office*